United States Patent

Chen et al.

[11] Patent Number: 5,932,248
[45] Date of Patent: Aug. 3, 1999

[54] CONTROLLED RELEASE PREPARATIONS FOR CYTOTOXIC OR CYTOSTATIC DRUGS

[75] Inventors: Yan Chen, Duncraig; Bruce Nathaniel Gray, Claremont, both of Australia

[73] Assignee: Paragon Medical Limited, Western Australia, Australia

[21] Appl. No.: 08/648,055

[22] PCT Filed: Nov. 17, 1994

[86] PCT No.: PCT/AU94/00708

§ 371 Date: Dec. 2, 1996

§ 102(e) Date: Dec. 2, 1996

[87] PCT Pub. No.: WO95/13798

PCT Pub. Date: May 26, 1995

[30] Foreign Application Priority Data

Nov. 18, 1993 [AU] Australia .............................. PM2492

[51] Int. Cl.[6] .............................. A61K 9/16; A61K 47/48
[52] U.S. Cl. .................... 424/486; 424/484; 424/488; 424/490; 424/494
[58] Field of Search ................................. 424/486, 451, 424/457, 484, 488, 490, 494

[56] References Cited

U.S. PATENT DOCUMENTS

| | | |
|---|---|---|
| 4,946,686 | 8/1990 | McClelland et al. . |
| 5,061,492 | 10/1991 | Okada et al. . |
| 5,100,668 | 3/1992 | Edelman et al. . |
| 5,271,945 | 12/1993 | Yoshioka et al. . |
| 5,288,496 | 2/1994 | Lewis . |

FOREIGN PATENT DOCUMENTS

| | | |
|---|---|---|
| 6058386 | 1/1987 | Australia . |
| B4430689 | 5/1990 | Australia . |
| 9211038 | 7/1992 | WIPO . |
| 9211844 | 7/1992 | WIPO . |
| 93/17668 | 9/1993 | WIPO . |

Primary Examiner—Thurman K. Page
Assistant Examiner—Brian K. Seidleck
Attorney, Agent, or Firm—Baker & Botts, LLP

[57] ABSTRACT

A controlled release preparation comprises an ionic polymer matrix loaded with an active compound, particularly a pharmaceutically active compound such as doxorubicin or other cytotoxic or cytostatic drug, the active compound being complexed with a complexing agent such as a metal ion to modify the release of the active compound from the polymer matrix. The ionic polymer matrix may be provided in the form of microspheres, such as microspheres of crosslinked albumin/dextran sulphate.

14 Claims, 8 Drawing Sheets

CONTROLLED RELEASE PREPARATIONS FOR CYTOTOXIC OR CYTOSTATIC DRUGS

This application is a 371 PCT/AU94/00708, filed Nov. 17, 1994.

FIELD OF THE INVENTION

This invention relates to the controlled release of active compounds, particularly pharmaceutically active compounds. More particularly, it relates to the use of the interaction of a complexing agent with a pharmaceutically active compound or other active compound as a release control mechanism, in combination with an ionic polymer supporting matrix, for example to improve targeting of the pharmaceutically active compound to the desired site of action of the compound.

BACKGROUND OF THE INVENTION

In its broadest aspect, the present invention extends to a preparation for the controlled release of any chemical compound which has a particular activity, for example in the industrial or agricultural fields as well as in the medical and veterinary fields.

The present invention is described in detail herein with particular reference to the targeting of cytotoxic or cytostatic drugs, particularly the anticancer drugs doxorubicin (DOX) and cisplatin (CDDP), to a tumour site in a human or animal patient, however it will be understood that the present invention is not restricted to delivery of these particular anticancer drugs and in one preferred aspect extends to the delivery of any pharmaceutically active compound. As noted above, in its broadest aspect this invention extends to the controlled release of active compounds in general.

The incorporation of active cytotoxic drugs into controlled release matrices has been demonstrated to have potential useful applications for the treatment of cancer. These drug-polymer complexes can be administered by either direct injection into the tumour, or by embolisation in the form of microspheres into the arterial circulation of the target organ containing the tumour. Both embolisation into the arterial circulation and direct injection into solid tumour deposits are recognised forms of regional cancer therapy[1,2]. In the situation where the drug-polymer complex is embolised into the arterial circulation of a cancer bearing organ, the drug-polymer complex is manufactured in the form of small particles or microspheres, usually in the size range of 10–200 micron in diameter. When the drug-polymer complex is administered directly into the tumour, the same formulation may be used but without the necessity to form microspheres.

There are two basic requirements for this form of therapy to be effective. First, there is a need to localise sufficient quantities of the drug at the target site to have the desired cytotoxic effect. Second, there is a need to control the rate of delivery into the tumour milieu that will cause maximal cell destruction. To achieve these, it is essential to design or develop a polymer matrix system that can carry a high load of cytotoxic drug as well as provide a controlled or sustained drug release profile.

This often poses a problem for the formulation of sustained release matrices. It is frequently observed that matrices with a high drug loading release the drug rapidly, known as a "burst release" effect. This is most likely a result of weak bonding or superficial location of drug during the formulation of the high loading matrix. The conventional approach of using a coating technique may sustain the release of drug, but usually decreases the drug loading of the system[3].

In the treatment of patients with cancer using regional chemotherapy, it is desirable for the drug-polymer complex to be degradable so that repeated doses can be given. Therefore, it is necessary to also construct a drug-polymer complex that will degrade within the tissues of the body.

For a sustained/controlled release system, the rate of drug release is determined to a large extent by the interaction between the drug and polymer matrices which is influenced by the method of drug incorporation. Drugs usually can be incorporated into the controlled release systems by the following simplified means: physical entrapment, ionic interaction and covalent binding. Physical entrapment allows medium to high drug loading but usually drug releases too rapidly. Ionic interaction can also give good drug loading but burst release can still be a problem. Covalent binding results in low drug loading and slow release rate. For biodegradable polymer matrices, the rate of degradation will also influence the drug release rate in vivo.

Doxorubicin (DOX), an anthracycline, is one of the most widely used drugs for the treatment of cancer. However, systemic administration of this agent can result in cardiotoxicity and other tissue damage and this has led to attempts to develop systems which target DOX more directly to the tumour site. One of the most promising of these is to inject microspheres containing DOX into the vasculature supplying the tumour with the intent that the microspheres become embolised and then release their drug, over a sustained period of time, into the environment of the tumour.

The original approach was to use microspheres prepared by polymerising albumin in the presence of DOX[4-8] but these particles suffered from the disadvantages of having low loading capacities (1–13%) and an initial burst release profile. The inclusion of polyanionic compounds such as poly α-L-glutamic acid[9], poly β-L aspartic acid[10] or heparin[11] into the formulation of albumin microspheres has improved these loading and release characteristics to some extent. An alternative approach has been to use commercially available anion-exchange resins containing sulphonic acid groups to bind DOX[12,13]. These particles demonstrate high loading capacities and excellent release characteristics and have shown considerable promise in treating rat liver and rat hind limb tumours[14,15]. However, although non-toxic, these microspheres do not appear to degrade in vitro or in vivo which may limit their use in those patients where further applications of drug treatment are necessary.

One object of the work leading to the present invention has been to provide a system with high drug loading, sustained release but minimum burst release effect and biodegradability. In one aspect of this work, the present inventors have developed a biodegradable ionic polymer as the matrix, and used an ionic interaction as the drug-polymer binding mechanism which has achieved a high drug loading. The inventors have also developed the formation of drug-metal ions complexes to suppress the burst release. This has resulted in a carrier matrix with all the required properties for clinical use.

DESCRIPTION OF THE INVENTION

Figure 1:
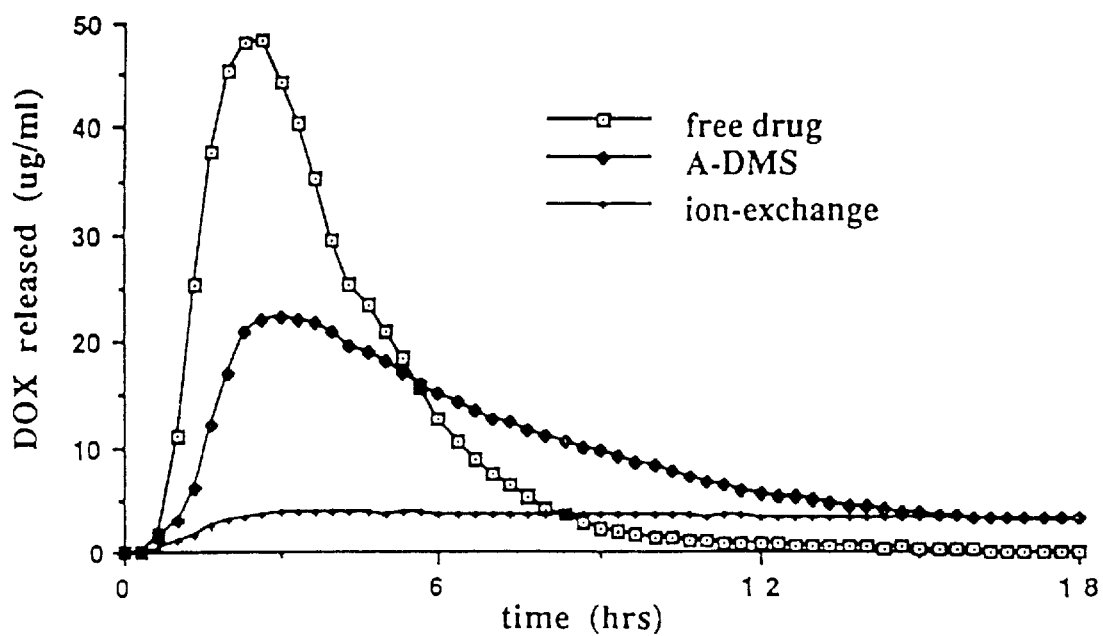
FIG. 1 shows the release profile of maximally loaded A-DMS (DOX payload of 78%) eluted with PBS using the continuous method and comparisons with ion-exchange resin (DOX payload of 63%) and free drug. Each procedure used 1 mg of DOX.

According to the present invention, there is provided a controlled release preparation comprising an ionic polymer matrix loaded with an active compound, for example a pharmaceutically active compound, said active compound being complexed with a complexing agent to modify the release of the active compound from the polymer matrix.

As used throughout this specification and the claims which follow, the term "pharmaceutically active compound" is to be understood as encompassing compounds which have therapeutic activity and which are used in either or both of the human pharmaceutical and veterinary fields.

Preferably, the ionic polymer matrix is provided in the form of microspheres, for example microspheres in the size range of 10–200 micron in diameter, and preferably in the range of 20–70 micron in diameter. Such microspheres are particularly appropriate where the controlled release preparation comprises a pharmaceutically active compound and is to be administered parenterally, for example intravenously, intraarterially or by direct injection. It is to be understood, however, that the controlled release preparation of this invention can be applied to or incorporated into other types of formulations or drug delivery systems such as suspension, emulsion, liposome, nanoparticle, microcapsule/microparticle, conjugate/aggregate, implant, disc, film and membrane delivery systems.

In essence, the present invention involves the complexing of the active compound in the supporting ionic polymer matrix as a mechanism to control the release of the active compound. Experimental results using pharmaceutically active compounds demonstrate that this complexing results in many advantages over other drug-matrix formulations, including high loading reduction of initial burst release of active compound, control of release of active compound, and biodegradability.

In accordance with one particular aspect of the present invention, the drug-metal ion complexation has been developed to minimise burst release without affecting the favourable high drug loading of the system. It is known that certain metals have affinity to drugs as well as to polymers[16]. In some cases, the drug-metal complexes can be biologically active. DOX-iron is an example[17]. However, drug-metal ion complexation has not been proposed before as a control release mechanism for drugs. In this regard, it should be noted that the present invention is not directed to the controlled release of DOX-iron, but rather the use of the formation of DOX-metal ion and DOX-metal ion-polymer complexes as a control release mechanism to provide a system with optimum/desirable release of native DOX. Based on the experimental data herein, it appears that the complexation of metal ions with DOX, and especially weakly bound DOX, forms a macromolecule network within the polymer matrices. This results in the slow release of DOX. Because the amount of metal ions required to form the complexes is very small, initial drug loading is not affected by this technique. Use of different ratios and types of metal ions allows the formulation of a matrix system with versatile and sustained drug release profiles, while at the same time maintaining the high level of drug loading.

In one preferred aspect of this invention, microspheres of crosslinked albumin and dextran sulphate are used as polymer matrices for ionic drugs such as DOX and CDDP, providing both the supporting structure and anionic sites for the cationic drugs DOX and CDDP to achieve high drug loading. In this embodiment, albumin and dextran sulphate represent two groups of polymers, one providing the supporting network and the other being a potential ionic exchanger. Both albumin and dextran sulphate can be replaced by other polymers which have the similar properties, such as by transferrin and chondroitin sulphate, respectively. In some cases, the two polymers can also be replaced by one polymer system which can provide both supporting and ionic binding functions, such as an ion exchange resin, for example polystyrene-divinylbenzene based ion exchange resin or SP-Sephadex. The same principle can also be applied to formulations of polymer matrices for anionic drugs, by employing polymers containing cationic groups.

The ionic polymer matrix of the controlled release preparation of this invention may be biodegradable or non-biodegradable. Examples of non-biodegradable polymer matrices are the ion exchange resins such as polystyrene-divinylbenzene based ion exchange resin as described above.

The polymer matrix comprising crosslinked albumin and dextran sulphate described above is one example of a biodegradable polymer matrix. In such a matrix, dextran sulphate is used as an ionic agent to form an ionic polymer matrix to interact with and control the release of active compounds containing cationic groups. Examples of other ionic agents that can be used instead of dextran sulphate include amylopectin sulphate, carrageen, chondroitin sulphate, heparin sulphate, heparin, fucoidan, polyaspartic acid, polyglutamic acid, polyinosinic acid, polylactic acid, polyvalent polymeric acids, SP-Sephadex, CM-Sephadex, dextran sulphate cellulose, dextran sulphate agarose, cationic ion-exchange resins and any other agents that contain acidic/anionic groups.

Albumin such as bovine or human serum albumin may be used in the biodegradable ionic polymer matrix as a supporting material. Various other supporting materials may be used instead of albumin in these matrices, including for example casein, gelatin, haemoglobin, transferrin, collagen, fibrinogen, fibrin, zein, ferritin, actin, and any other agent of similar nature that can form ionic polymer matrices with dextran sulphate or any ionic agent above.

Preferably, metal ions are used to complex the active compound loaded onto the ionic polymer matrices to modify and hence to control the release characteristics of the active compound. Examples of metal ions that can be used as complexing agents include iron, copper, zinc, cobalt, chromium, nickel, palladium, zirconium, titanium and vanadium. Other agents which can form a complex with the active compound, such as chitosan in the case of CDDP and other metal-based active compounds, may also be used.

The complexing agent is preferably one which will retard the release of the active compound. Where the active compound is DOX, this complexing agent is preferably the Fe ion.

As previously described, any suitable active compound may be loaded into the ionic polymer matrix in accordance with this invention, including pharmaceutically active compounds, for example cytotoxic or cytostatic drugs such as doxorubicin, daunorubicin and cisplatin.

It has been found that a polymer matrix comprising albumin-dextran sulphate microspheres (A-DMS) possesses high loading capacities with respect to DOX. The rate of release of DOX from these microspheres can be controlled by loading the microspheres to varying extents and by treating the loaded microspheres with different concentrations of iron to form a complex with DOX[17,18] which alters the binding of DOX to the microspheres.

In yet another aspect, this invention provides a pharmaceutical composition which comprises a controlled release preparation as broadly described above wherein the active compound is a pharmaceutically active compound, together with a pharmaceutically acceptable carrier and/or diluent.

The formulation of such pharmaceutical compositions is well known to persons skilled in this field. Suitable pharmaceutically acceptable carriers and/or diluents include any and all conventional solvents, dispersion media, aqueous solutions, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

In a further aspect, the present invention provides a method of treatment of a human or animal patient which comprises administration to the patient of a therapeutically effective amount of a controlled release preparation as broadly described above wherein the active compound is a pharmaceutically active compound. In this aspect, the invention also extends to the use of a controlled release preparation as broadly described above wherein the active compound is a pharmaceutically active compound in the manufacture of a pharmaceutical composition for use in treatment of a human or animal patient.

A variety of administration routes are available for use in the treatment of a human or animal patient. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the pharmaceutically active compound without causing clinically unacceptable adverse effects. Such modes of administration include parenteral (e.g. subcutaneous, intramuscular intraarterial and intravenous) routes.

Compositions suitable for parenteral administration conveniently comprise a sterile aqueous preparation of the active compound which is preferably isotonic with the blood of the recipient. The sterile injectable preparation may be a sterile injectable solution or suspension in a non-toxic parenterally-acceptable diluent or solvent. Among the acceptable vehicles and solvents that may be employed are water, Ringer's solution and isotonic sodium chloride solution.

The pharmaceutically active compound is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The detailed description herein demonstrates that biodegradable microspherical particles prepared by crosslinking an emulsion of albumin and high molecular weight dextran sulphate exhibit strong anion exchange properties. These microspheres have a high loading capacity for the cationic drugs DOX and CDDP. The release profiles of DOX from these microspheres can be varied by either altering the percentage loading or treating the drug-loaded microspheres with Fe(III), while the release profiles of CDDP can be varied by treating the drug-loaded microspheres with chitosan. This diversity in release profiles offers promise for using these microspheres in the clinical treatment of tumours.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

This Example demonstrates a technique for the manufacture of a degradable drug-complex system incorporating doxorubicin.

A. Materials and Methods

Bovine serum albumin was manufactured by Commonwealth Serum Laboratories, Melbourne, Australia. Dextran sulphate sodium salt (molecular weight 500,000) was obtained from Sigma (Ohio, USA). Doxorubicin was kindly provided by Farmitalia, Sydney, Australia. Ion-exchange resin, Aminex AG50WX4 (32.5±2.5 $\mu$m in diameter) from Bio-Rad was purified by washing with HCl and NaOH solutions and distilled water. All other chemicals used were analytical reagents.

Synthesis of Albumin-Dextran Sulphate Microspheres (A-DMS)

Bovine serum albumin (0.4 g) was dissolved in 1.6 ml of 1 mM phosphate buffer, pH 7.5, containing 0.1% sodium dodecyl sulphate and then was mixed with 2 ml of 20% (w/v) dextran sulphate sodium salt to form the disperse phase. The disperse phase was emulsified using a Silverson Mixer (Silverson Machines, Chesham, Bucks, UK) in 100 ml of olive oil at a stirring speed of 720 rpm at room temperature. An aqueous solution of glutaraldehyde (10% w/v, 400 µl) was added to the emulsion which was stirred for 1 h to crosslink the albumin and solidify the microspheres. The microspheres were isolated and washed with light petroleum (×3), isopropanol (×2) and distilled water containing 0.1% Tween 80 (×2). After centrifugation microspheres were filtered through a nylon mesh (63 µm) and a stainless steel sieve (20 µm). Microspheres within the size range 20–63 µm were washed with isopropanol (×2) then dried at 37° C. in an incubator for 48 h. They were stored at 4° C. in a desiccator until used.

Drug Loading

To obtain maximal loading the A-DMS, typically 20 mg, were treated with 100 µl of ethanol and washed with 3 ml of water to swell the microspheres. The swollen microspheres were then mixed with 2 ml of DOX solution (10 mg/ml) at 4° C. for 18 h in darkness. The microspheres were washed 3 times with 2 ml of water and the degree of loading was determined from the depletion of the DOX solution and the amount of DOX in the rinses. For less than maximal loading (20–60%) the calculated amount of DOX was mixed with the swollen microspheres for periods from 10 min to 1 h during which time uptake was greater than 99% and the red loading solution became almost colourless. DOX levels were determined by their UV absorption at 495 nm.

Treatment of DOX-Loaded A-DMS with Iron

A typical procedure to obtain maximal complexing with iron was as follows. The DOX-loaded A-DMS containing 10 mg of DOX were suspended in 1 ml of water and 200 µl of 0.1 mol/l Hepes buffer (pH 7.0) was added followed by 200 µl of 0.1 mol/l $FeSO_4$-$7H_2O$. The suspension was mixed for 5 min as the microspheres changed in colour from a deep red to a brown-black and the treated particles were then washed with water (3×3 ml) to remove buffer and excess $FeSO_4$. Iron-treated DOX microspheres were also prepared using a range of Fe to DOX ratios (1:1, 1:3, 1:6, 1:9, 1:12) in order to determine the effect of the degree of complexing on the release rate.

Release Studies

In vitro release of DOX from A-DMS was assessed using either a continuous flow system or a discontinuous system. For the flow system, microspheres containing DOX or iron-treated DOX (usually 1 mg of drug) were immobilised on a glass column and eluted at a rate of 5 ml/h with phosphate-buffered saline (PBS) with a composition of 0.15 mol/l NaCl, 0.05 mol/l $NaH_2PO_4$, pH 7.0 at 37° C. Concentrations of DOX in the eluant were continuously monitored by UV absorption at 495 nm. For the discontinuous system DOX loaded A-DMS were mixed with 3.5 ml of PBS on a rocking mixer for 20 min. the microspheres were sedimented by centrifugation and the supernatant was aspirated and its DOX content determined by UV absorption at 495 nm. Fresh PBS was added and the cycle was repeated for up to 6 h. Portions of the eluant from both methods were retained for characterisation by HPLC, UV spectroscopy and atomic absorption. The HPLC was performed using conditions previously described[13].

B. Results and Discussion

Synthesis of A-DMS

Microspheres, prepared from equal amounts by weight of albumin and dextran sulphate were obtained as a free flowing brown powder in yields of 32–40% for the diameter range 20–63 µm (sized by light microscopy).

Drug Loading

The A-DMS exhibited strong ion-exchange properties and loaded similar amounts of DOX to the commercial anion exchange resin containing sulphonic acid functional groups. These loadings (calculated as gs of drug loaded/100 g of empty microspheres) were greater than for previously reported albumin based microspheres (see Table 1). Submaximal loadings, obtained by using lower ratios of DOX to microspheres, were achieved with greatly reduced mixing times. The lowest loadings used in this study (20–25%) were complete in less than 5 min as evidenced by the total loss of colour from the initial deep red loading solution.

TABLE 1

Comparison of payloads of albumin (alb)-based microspheres.

| Source | % loading | Composition |
|---|---|---|
| Present invention | 78–99[a] | alb-dextran sulphate |
| Goldberg et al.[9] | 21–46[a,b] | alb-poly glutamic acid |
| Cremers et al.[11] | 25–30[a,b] | alb-heparin |
| Cremers et al.[11] | 7[a,b] | alb |
| Chen et al.[10] | 4[b] | alb-poly aspartic acid |
| Chen et al.[13] | 67–86[a] | ion exchange resin |

[a]DOX-loaded onto microspheres after preparation.
[b]loading calculated as % [drug/(drug + ms)]

Release of DOX from Maximally-Loaded A-DMS

Figure 2:
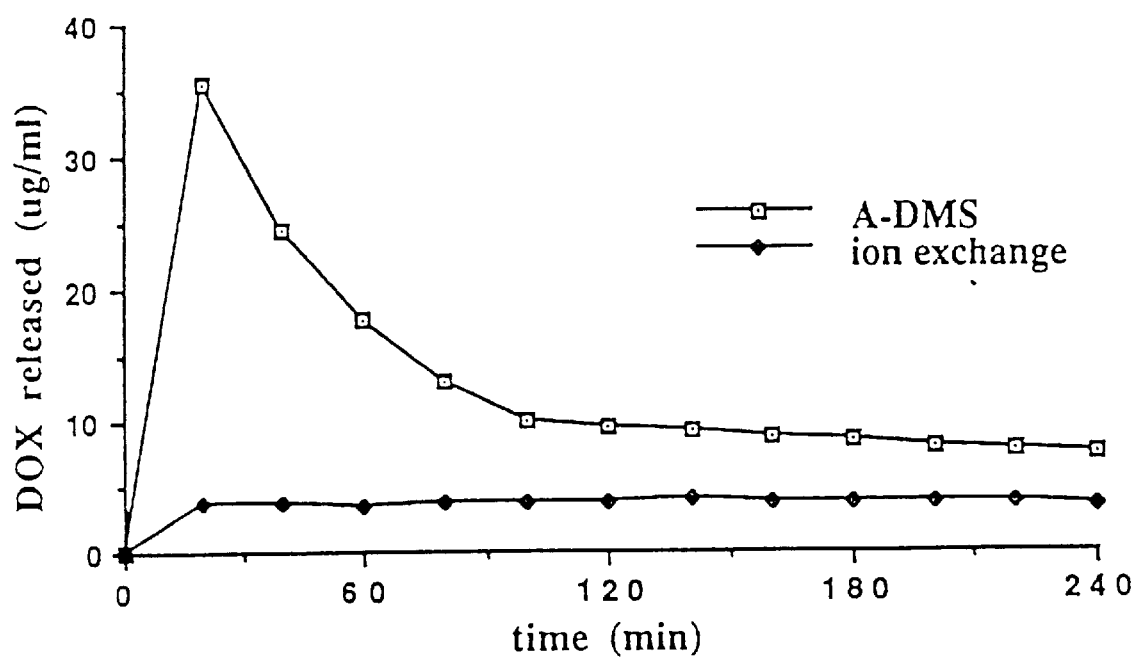
FIG. 2 shows the release profile of maximally loaded A-DMS (DOX payload of 80%) eluted with PBS using the discontinuous method and comparison with ion-exchange resin (DOX payload of 61%). Each procedure used 1 mg of DOX.
Figure 3:
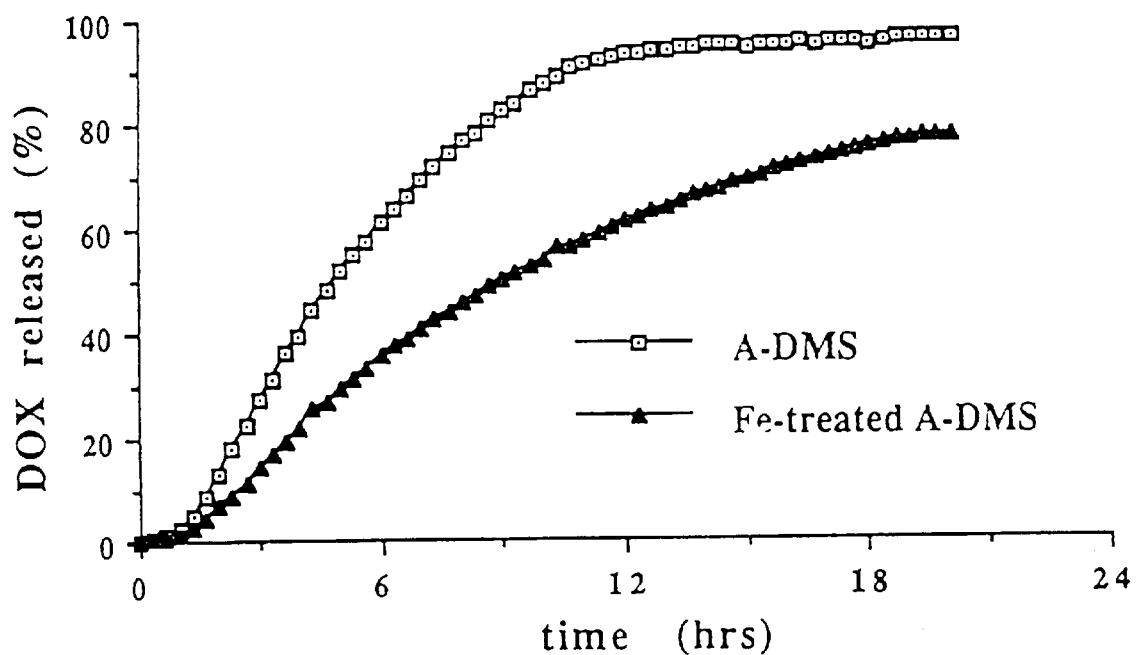
FIG. 3 shows the cumulative release of DOX from microspheres eluted with PBS using continuous method. Concentrations were determined by UV absorption.

Profiles for the release of DOX from maximally-loaded A-DMS and their comparison with ion-exchange microspheres are shown in FIGS. 1 and 2 for the continuous and discontinuous methods respectively. For this and for all other release studies performed, the two methods gave qualitatively very similar results. The release pattern for the A-DMS was characterised by an initial rapid loss of DOX from the microspheres followed by a more steady release rate. During the initial phase 43% of available drug was released (calculated from discontinuous study). This contrasts with the ion-exchange particles which had a more uniform release rate (12% released during the same time interval). In those experiments in which the loaded particles were repetitively extracted until no further DOX was released, 85–95% of DOX was recoverable from the A-DMS (calculated from UV absorption at 495 nm). A graph of the cumulative release of drug from DOX loaded A-DMS is shown in FIG. 3.

Effect of Varying Payloads on Release Rate

Figure 4:
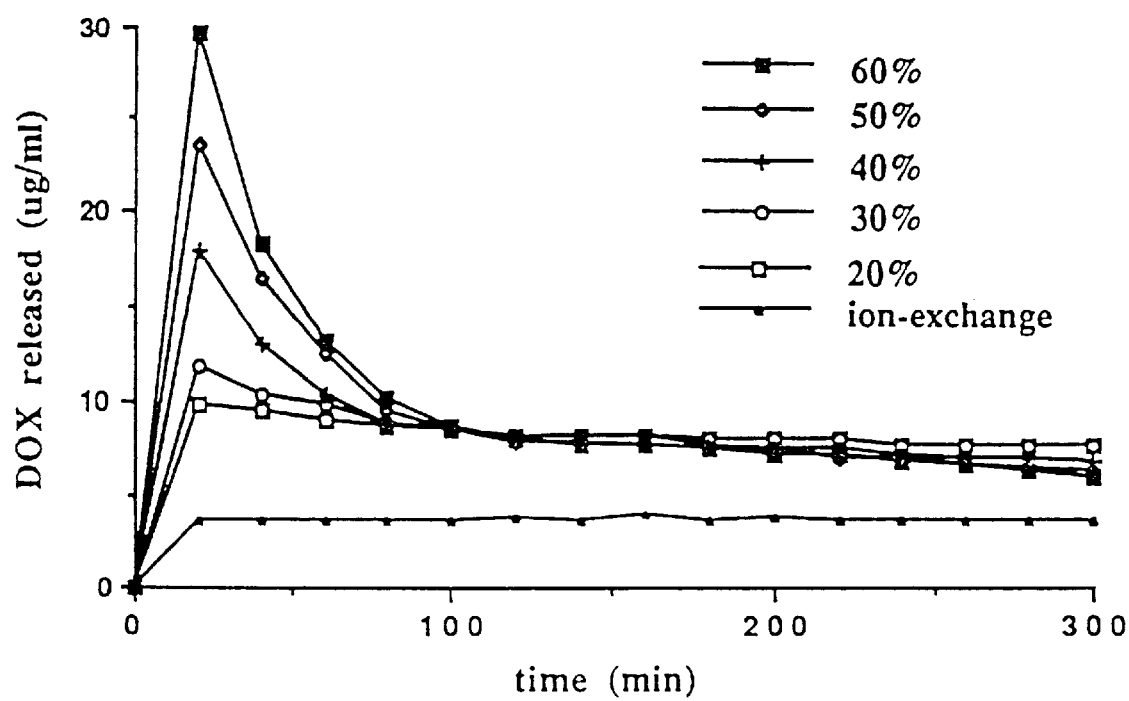
FIG. 4 shows the release profiles of sub-maximally loaded A-DMS (DOX payloads of 20–60%) eluted with PBS showing effect of reduced loadings on "burst release" as determined by the discontinuous method. Each procedure was based on 1 mg of DOX.

As burst release profiles are generally clinically undesirable due to increased toxicity, studies were performed which were aimed at reducing the initial high release rate from the A-DMS. The effect of reducing the loading is shown in FIG. 4. There was a graded reduction in the burst release phenomena as the loadings were reduced from 60 to 20%. This led to the observation that the lowest loaded microspheres actually released at a greater rate than the higher loadings towards the end of the study as the higher loaded microspheres were becoming drug depleted. Although the 20 and 30% loaded A-DMS released DOX at a steady rate, a possible disadvantage of using these loadings clinically would be the greater number of microspheres needed to deliver an equivalent amount of drug. However these low loadings still compare favourably with previously published values for albumin-based microspheres while exhibiting better release profiles. The most favourable loading for clinical use would need to be determined experimentally.

A likely explanation for these observations of the effect of loading on the release rate is that the A-DMS contain binding sites of varying strengths. At low loadings the strongest sites would be preferentially occupied and would release their drug at a slower rate. At saturation loading even the weakest sites would be occupied and drug from these sites could be rapidly lost resulting in the "burst release".

Effect of Iron Treatment on Release Rate from A-DMS.

Figure 5:
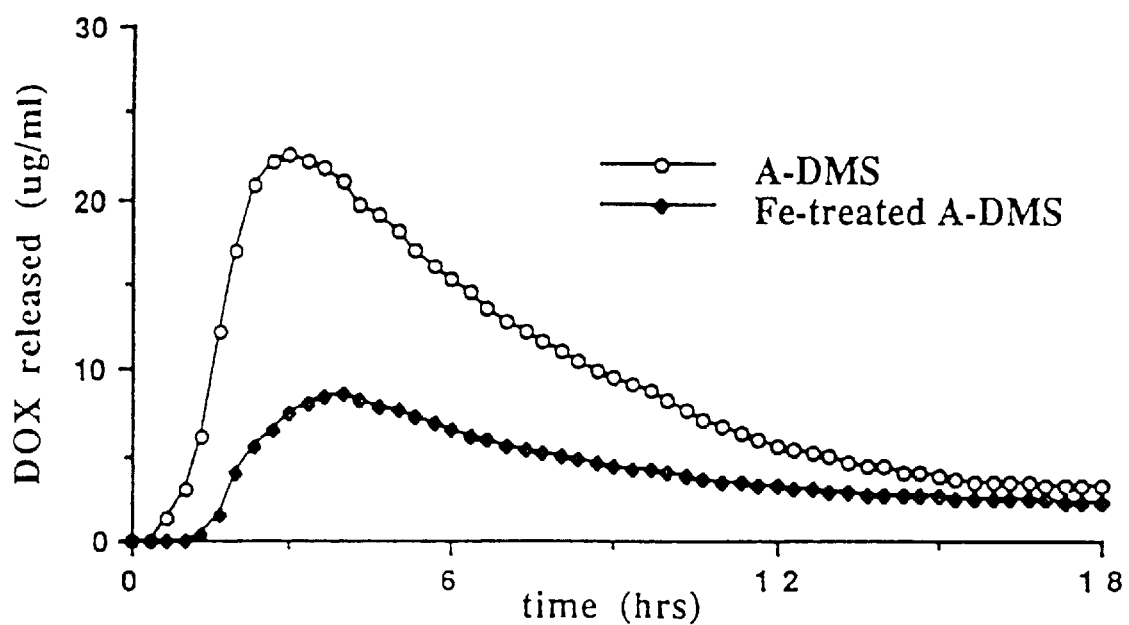
FIG. 5 shows the release profiles of maximally loaded A-DMS (DOX payload of 80%) before and after iron treatment. Microspheres were eluted with PBS using the continuous method. Each procedure used 1 mg of DOX.
Figure 6:
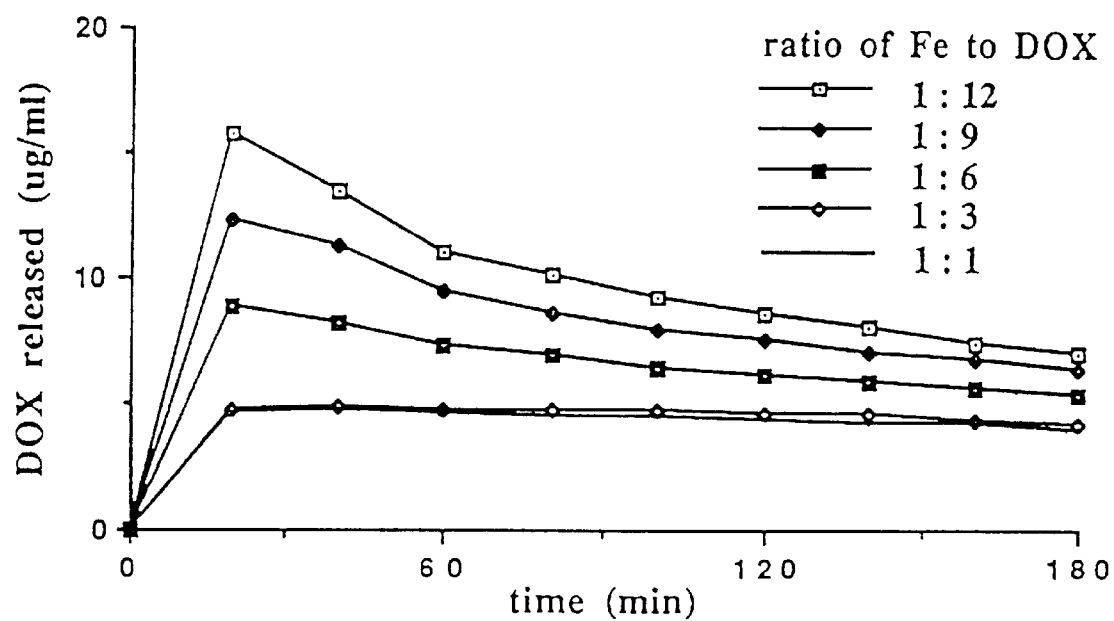
FIG. 6 shows the release profiles of A-DMZ (DOX payload of 50%) eluted with PBS showing effect of treatment of iron at different Fe (III) to DOX ratios as determined by the discontinuous method. Each procedure used 1 mg of DOX.

DOX is known to form complexes with some metals in solution including iron (one molecule of Fe (III) combines with three of DOX), and it has been shown that the release rate of DOX from ion-exchange microspheres can be reduced following treatment of the loaded microspheres with iron or copper solutions (see Example 4 hereunder). It was therefore decided to investigate whether iron treatment of DOX-loaded A-DMS would have a similar effect especially as it is well known that iron also forms a complex with dextran. Although in this study iron was added to the microspheres as Fe(II), under the experimental conditions it is rapidly oxidised to Fe(III) and it is this state of iron which is believed to complex with DOX. The effect on the release rate of treating maximally loaded DOX A-DMS with 1 parts iron to 1 part DOX (6-fold stoichiometric excess of iron) using the continuous flow method is shown in FIG. 5. The effect of treatment of 50% loaded A-DMS using a range of De to DOX ratios (1:1 to 1:12) was determined using the discontinuous system with the results shown in FIG. 6. Both sets of experiments show that treatment using an Fe to DOX ratio of 1:3 or greater has a marked effect on overcoming the burst release phenomenon as well as reducing the release rate relative to untreated microspheres. The release profiles of the Fe treated DOX A-DMS and the untreated DOX ion-exchange microspheres are quite similar (compare FIGS. 1 and 5 or 2 and 6).

To determine the amount of DOX available for release from the iron-treated microspheres, they were extracted with PBS over a 2 h period. Up to 78% of loaded drug was recoverable during extraction (see FIG. 3) and a further 4–9% became available from partial digestion of the extracted microspheres with papain.

Characterisation of the Release Product
(a) From DOX-Loaded A-DMS

Concentrations of DOX in release fractions were determined by both UV absorbance which measures all chromophores absorbing at 495 nm and by an established HPLC method, which resolves DOX from its UV absorbing metabolites. HPLC values for DOX were 85–95% of those determined using total UV absorption, although there was no evidence of any of the known DOX metabolites to account for this discrepancy. As 5–15% of DOX on the microspheres is not readily extracted, 72–90% of the original payload should be available therapeutically as active DOX.
(b) From iron treated DOX-loaded A-DMS.

To determine whether DOX was released as a 1:3 iron-DOX complex or as free DOX, the release fractions were assayed for iron content in addition to the above. Although iron was detected, stoichiometrically the amount was less than a third of that estimated for a true complex, also the complex is reported to absorb strongly at 612 nm but no significant absorption was observed at this wavelength for any of the release fractions. Even if DOX was released as an iron-DOX chelate, at the concentrations achieved in this study it would be expected to dissociate as it has previously been shown that on dilution the complex dissociates into its components[17]. It was therefore concluded that iron treated DOX-loaded A-DMS releases the large majority of its "DOX" in the free form.

By HPLC, 70–85% of the UV absorbing material at 495 nm could be accounted for as free DOX. Therefore, considering the amount of DOX that could be extracted from the microspheres following iron treatment, then 52–66% of loaded drug should be readily available as active DOX with the possibility of up to a further 9% being released on biodegradation of the microspheres.

Stability of A-DMS to Storage

A-DMS which had been stored desiccated at 4° C. for up to 4 months showed similar loading and release characteristics to freshly prepared microspheres. DOX-loaded A-DMS which were stored at −20° C. as a frozen suspension in water showed no degradation when used in release studies after 1 month.

EXAMPLE 2

Figure 7:
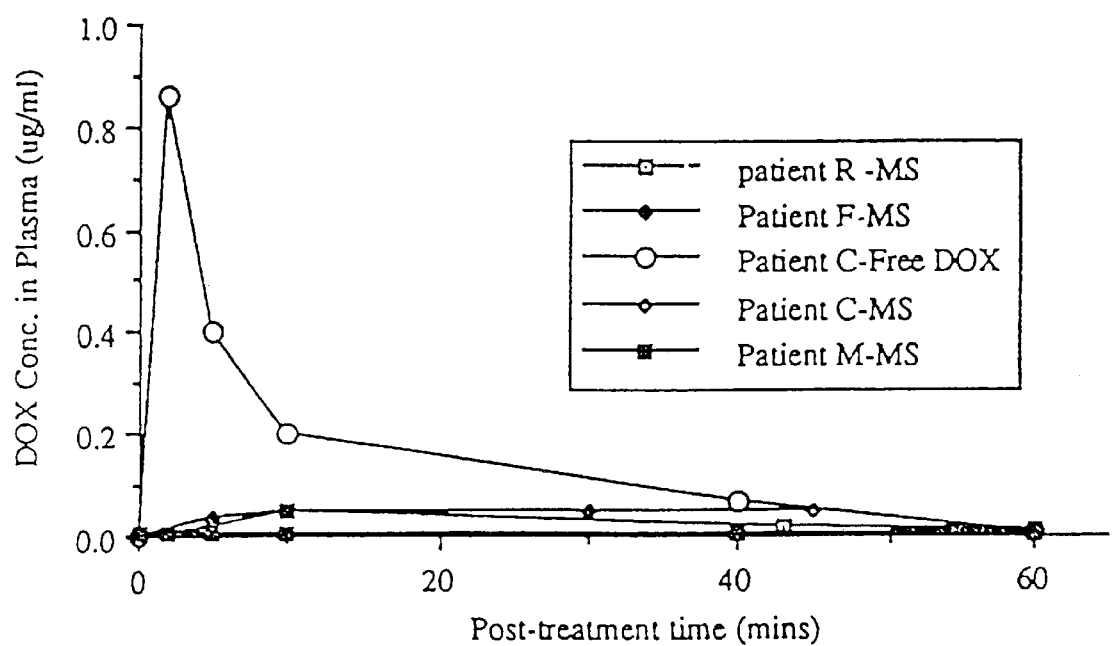
FIG. 7 shows the plasma levels of doxorubicin in patients receiving treatments of free DOX and DOX-loaded iron-treated A-DMZ (1 mg/kg patient body weight).

In order to demonstrate the results of in vivo use of iron-treated DOX-loaded A-DMS prepared as described in Example 1 above, the microspheres were administered to four patients (patients R, F, C and M) with liver cancer. The dose of microspheres administered was 1 mg/kg of patient body weight and was injected into the hepatic artery of each of the four patients. Systemic blood plasma levels were taken over a period of 60 minutes following the injection. The results are shown in FIG. 7 and indicate that virtually no doxorubicin was detectable in the systemic circulation following injection of the DOX-loaded A-DMS into the hepatic artery. One patient (patient C) also had free doxorubicin injected into the hepatic artery, following which high levels of the drug were found in the systemic circulation. These results demonstrate that A-DMS-bound doxorubicin is retained in the target organ into which the microspheres are delivered.

EXAMPLE 3

This Example demonstrates a technique for the manufacture of both degradable and non-degradable drug-complexes using DOX, as well as an v therapeutic evaluation of the DOX-loaded complexes.

Polystyrene-divinylbenzene based ion exchange resin (IE resin, 32.5±2.5 $\mu$m) and albumin-dextran sulphate microspheres (A-DMS, 29.4±8.0 $\mu$m) were chosen as drug carriers for DOX. IE resin was purified by washing with HCl and NaOH solution and deionised water. DOX was loaded onto ion-exchange microsphere resin using a batch manufacturing process. Briefly, prepurified ion exchange resin was mixed with pure DOX solution (10 mg/ml) in a 1:1 ratio by weight, at room temperature overnight. The DOX-loaded IE resin microspheres were then separated from the drug supernatant by centrifugation and washed twice with deionised water before being resuspended in a known volume of deionised water.

The technique described in Example 1 was used to formulate the DOX-loaded A-DMS microspheres.

The drug release studies of both IE resin and A-DMS with and without metal ion complexation were conducted using either a continuous system with constant elution or a discontinuous system with batched elution with phosphate buffered saline (PBS) as the release medium.

In order to assess the therapeutic effect of the drug-loaded microspheres, testing was performed using WAG male rats with colonic carcinoma implanted in their livers. Eight days after tumour implant, rats were randomly divided into groups with minimum 5 rats per group. The rats received treatments of free DOX solution or different microsphere systems via hepatic artery administration at a dose of 2.5 mg/kg. One week after the treatment, all animals were sacrificed, their livers removed and tumour weight measured. During the treatment period, the body weights of animals were monitored regularly. The statistical analysis of significant difference between groups was conducted using analysis of variance for comparing multiple samples with unequal size.

Both IE resin and A-DMS show favourable high loading capacities for DOX, with maximum loading of 67–86% (mg DOX/100 mg empty microspheres) and 75–100% respectively. This is believed due to a similarity in functional groups between the two microspheres with IE resin possessing a sulphonic acid group and A-DMS, a sulphate group. Thus, they form ionic binding with cationic amine groups in DOX molecules resulting in high drug loading.

IE resin and A-DMS show very different release characteristics despite that they have similar drug loading capacities. IE resin provides a slow and constant drug release, whereas A-DMS displays a burst release although its level is very much lower than that of free DOX in solution. This could be caused by the weak ionic interaction between DOX and sulphate group in A-DMS. However, the same microspheres after treatment with ferric ion (Fe: DOX=3:1 molar ratio) released DOX much slower with almost no burst release. The release profiles of the Fe treated DOX A-DMS and untreated IE resin are quite similar.

Figure 8:
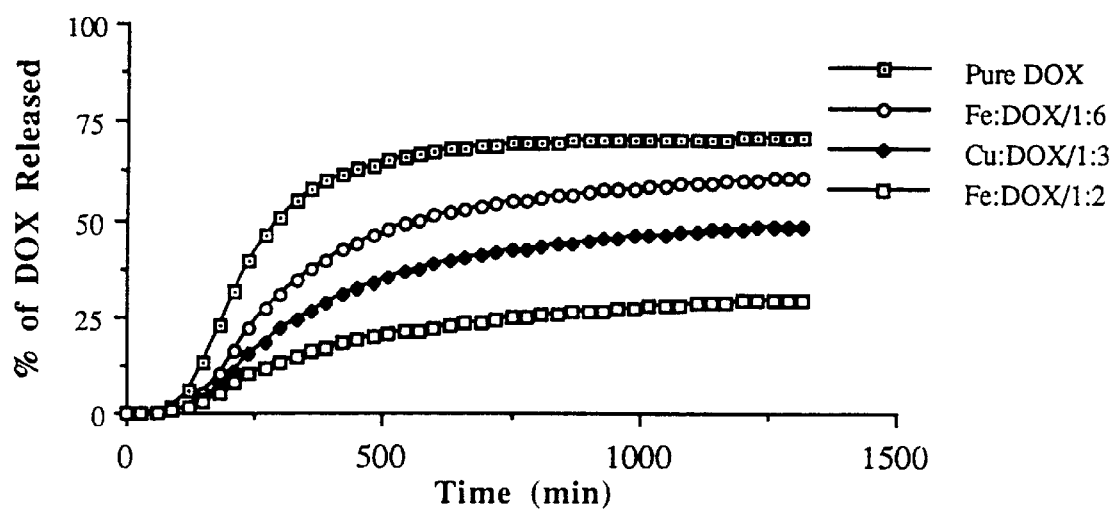
FIG. 8 shows the release profiles of Fe- and Cu-treated DOXS-loaded IE resins using PBS containing EDTA as release medium.

It was also found that both Fe and Cu could form complexes with DOX loaded IE resin MS resulting in slower and versatile drug release as shown in FIG. 8 with PBS containing EDTA as release medium. Thus, Fe treatment has provided a means of reducing the burst release and providing versatile controlled release profiles without affecting the drug loading.

FTIR studies of these microspheres indicate that the chemical interaction between DOX and metal ions has occurred resulting in the formation of complexes which delayed the release of DOX. Comparison of UV and HPLC measurement of release fractions of the Fe-treated DOX A-DMS indicates that 70–85% of DOX is released in its native form. AA analysis detected only trace iron, equivalent to 3–6% for a true complex. It is speculated that dissociated Fe may interact more strongly with the sulphate groups, and therefore stay on microspheres, while DOX is released into the medium.

Table 2 summarises the results obtained when three types of microspheres were examined for DOX delivery. It will be seen that the maximum drug loadings were similar for all three types, however they differ greatly in drug release and A-DMS release drug 3–4 times faster than the other two types. Both IE resin and FE-treated A-DMS release slowly and relatively constantly, however IE resin is non-degradable. In terms of reduction of tumour growth, in comparison to free DOX treatment the Fe-treated A-DMS exhibited most effectiveness at the significant level of $p<0.05$.

TABLE 2

Summary of microsphere systems.

| Microspheres | % Drug loading (mg/100 mgMS) | Drug Release | Biodegradability | Tumour Growth (%) MS/Free DOX |
|---|---|---|---|---|
| IE resin | 67–86% | + | − | 60% |
| A-DMS | 75–100% | +++ | + | 102% |
| Fe-A-DMS | 75–100% | + | + | 38% |

This study clearly demonstrates the importance of sustained drug release in improving the therapeutic efficacy of DOX. The use of Fe complexation with DOX significantly improved the degree of control of drug release and suppressed the burst release of drug from microspheres while maintaining the favourable drug loading. This results in important enhancement of DOX therapeutic efficacy, demonstrating that the concept of using drug-metal ion interactions is therapeutically most effective for treating cancer when the drug complex is administered as regional chemotherapy.

EXAMPLE 4

This Example demonstrates the application of the concept of drug-metal ion complexation to the formulation of sustained release systems for metal based drugs. Here, the metal based drug, cisplatin, is complexed with the polymer matrix albumin-dextran sulphate and chitosan.

Cisplatin was loaded onto polystyrene-divinylbenzene based ion-exchange resin (IE resin) using the same batch manufacturing process as described in Example 3 except 1 mg/ml pure cisplatin solution was used to mix with the resin.

To obtain cisplatin-loaded A-DMS, the albumin/dextran-$SO_4$ microspheres prepared by the method described in Example 1 were wetted with 2% ethanol before being mixed with an equal amount of cisplatin solution (1 mg/ml) overnight at room temperature. The incorporation of cisplatin into A-DMS was accomplished after separation of unbound drug from microspheres by centrifugation and subsequent washing of microspheres with deionised water.

CDDP-loaded IE resin and A-DMS were mixed with 1.5% chitosan solution (in 5% acetic acid) in 1:5 ratio by weight (cisplatin:chitosan) overnight at room temperature. The microspheres were then washed with deionised water, centrifuged and used immediately for the release studies.

The two microsphere formulations exhibited very different release profiles although they had the similar load of CDDP (45.7±8.7% and 46.1±12.4% respectively). IE resin released the drug markedly faster with approximately 60% of cisplatin released in the first 5 hr. In comparison, A-DMS only had nearly 20% of CDDP released in the same period. The treatment of microspheres with chitosan delayed the release of CDDP from IE resin in its later release phase but showed almost no effect on the initial release kinetics of A-DMS when measured using a continuous flow-through release system. It did, however, suppress the initial burst release of cisplatin from A-DMS in a closed release system.

Persons skilled in this art will appreciate that variations and modifications may be made to the invention as broadly described herein, other than those specifically described without departing from the spirit and scope of the invention. It is to be understood that this invention extends to include all such variations and modifications.

REFERENCES

1. Kerr, D. J., Willmott, N., McKillop, J. H. et al. Target organ disposition and plasma pharmacokinetics of doxorubicin incorporated into albumin microspheres after intrarenal arterial administration. *Cancer,* 62 (1988), 878.
2. Orenberg, E. K., Miller, B. H., Greenway, H. T. et al. The effect of intralesional 5-fluorouracil therapeutic implant (MPI 5003) for treatment of basal cell carcinoma. *J. Am. Acad. Dermatol.* 27 (5pt1) (1992), 723.
3. Irwin, W. J., Belaid, K. A. and Alpar, H. O. Drug delivery by ion exchange: IV coated resinate complexes of ester pro-drugs of propranoiol. *Drug. Dev. Ind. Pharm.* 14 (1988), 1307.
4. Senyei, A. E., Driscoll, C. F. and Widder, K. J. Biophysical drug targeting: magnetically responsive albumin microspheres. *Methods Enzymol.* 112 (1985), 56–67.
5. Longo, W. E. and Goldberg, E. P. Hydrophilic albumin microspheres. *Methods Enzymol.* 112 (1985), 18–27.
6. Gupta, P. K., Gallo, J. M., Hung, C. T. and Perrier, D. G. Influence of stabilisation temperature on the entrapment of adriamycin in albumin microspheres. *Drug Dev. Ind. Pharm.* 13 (1987), 1471–1482.
7. MacArdle, C. S., Lewi, H., Hansell, D., Kerr, D. J., McKillop, J. and Willmott, N. Cytotoxic-loaded albumin microspheres: a novel approach to regional chemotherapy. *Br. J. Surg.* 75 (1988), 132–134.
8. Jones, C., Burton, M. A. and Gray, B. N. Albumin microspheres as vehicles for the sustained and controlled release of doxorubicin. *J. Pharm. Pharmacol.* 41 91989), 813–816.
9. Goldberg, E. P. Iwata, H. and Longo. W. Hydrophilic albumin and dextran ion-exchange microspheres for localised chemotherapy. In: S. S. Davis, L. Illum, J. G. McVie and E. Tomlinson (Eds.) Microspheres and Drug Therapy. Pharmaceutical, Immunological and Medical Aspects, Elsevier, Amsterdam 1984, pp. 309–325.
10. Chen, Y. Willmott, N., Anderson, J. and Florence, A. T. Haemoglobin, transferrin and albumin/polyaspartic acid as carriers for the cytotoxic drug adriamycin. Ultrastructural appearance and drug content. J. Controlled Release, 8(1988), 93–101.
11. Cremers, H. F. M., Feigen, J., Kwon, G., Bae, Y. H., Kim, S. W., Noteborn, H. P. J. M. and McVie, J. G. Albumin-heparin microspheres as carriers for cytostatic agents. *J. Controlled Release,* 11 (1990), 167–179.
12. Jones, C., Burton, M. A. and Gray, B. N. In vitro release of cytotoxic agents from ion exchange resins. *J. Controlled Release,* 8 (1989), 251–257.
13. Chen, Y., Burton, M. A., Codde, J. P., Napoli, S., Martins, I. J. and Gray, B. Evaluation of ion-exchange microspheres as carriers for the anticancer drug doxorubicin: in vitro studies. *J. Pharm. Pharmacol.* 4 (1992), 211–215.
14. Codde, J. P., Lumsden, A. J., Napoli, S., Burton, M. A. and Gray, B. N. A comparative study of the anticancer efficacy of doxorubicin carrying microspheres and liposomes using a rat liver tumour model. *Anticancer Res.* 13 (1993), 539–544.
15. Burton, M. A., Jones, C., Trotter, J. M., Gray, B. N. and Codde, J. P. Efficacy of ion-exchange resins for antitumour drug delivery. *Reg. Cancer Treat.* 3 (1990), 36–39.
16. Lee, V. A., Musin, R. I., Tashmukhamedov, R. I. et al. Metal complexes of polymers with amino acid residues, formation, stability and controlled biological activity. *J. Controlled Release,* 14 (1990), 61.
17. Gelvan, D. and Samuni, A. Reappraisal of the association between adriamycin and iron. *Cancer Res.* 48 (1988), 5645–5649.
18. Beraldo, H., Garnier-Suillerot, A., Tosi, L. and Lavelle, F. Iron (III)-adriamycin and iron (III)-daunorubicin complexes: physiochemical characteristics, interaction with DNA and antitumour activity. *Biochemistry,* 24 (1985), 284–289.

We claim:

1. A controlled release preparation comprising an ionic polymer matrix loaded with a pharmaceutically active compound which is a cytotoxic or cytostatic drug, said pharmaceutically active compound being complexed with a metal ion to slow the release of the active compound from the polymer matrix.

2. A preparation according to claim 1, wherein the ionic polymer matrix is in the form of microspheres.

3. A preparation according to claim 2, wherein the microspheres have a diameter in the size range of 10–200 micron.

4. A preparation according to claim 1, wherein the cytotoxic or cytostatic drug is doxorubicin or daunorubicin.

5. A preparation according to claim 1, wherein the ionic polymer matrix comprises a biodegradable crosslinked albumin/dextran sulphate matrix.

6. A preparation according to claim 1, wherein the metal ion is Fe.

7. A preparation according to claim 1, wherein the ionic polymer matrix is selected from the group consisting of a crosslinked albumin/dextran sulphate matrix and a polystyrene-divinylbenzene based ion exchange resin, and the ionic polymer matrix is loaded with Fe-complexed doxorubicin.

8. A controlled release preparation comprising an ionic polymer matrix loaded with cisplatin, said cisplatin complexed with chitosan to slow the release of the cisplatin from the ionic polymer matrix.

9. A preparation according to claim 8, wherein the ionic polymer matrix is selected from the group consisting of a crosslinked albumin/dextran sulphate matrix and a polystyrene-divinylbenzene based ion exchange resin.

10. A pharmaceutical composition comprising a controlled release preparation according to claim 1 or claim 8, together with a pharmaceutically acceptable carrier and/or diluent.

11. A method of treatment of a human or animal patient, which comprises administration to the patient of a therapeutically effective amount of a controlled release preparation according to claim 1 or claim 8.

12. A method according to claim 11, wherein said controlled release preparation is administered parenterally.

13. A preparation according to claim 3, wherein said microspheres have a diameter in the size range of 20–70 micron.

14. A method according to claim 12, wherein said controlled release preparation is administered intraarterially or intravenously.

* * * * *

UNITED STATES PATENT AND TRADEMARK OFFICE
CERTIFICATE OF CORRECTION

PATENT NO. : 5,932,248
DATED : August 3, 1999
INVENTOR(S) : Chen et al.

It is certified that error appears in the above-identified patent and that said Letters Patent is hereby corrected as shown below:

Title page, Column 1. [73] Assignee: "Western Australia," should read -- Perth, --;

Column 14, line 18, "claim 1," should read -- claim 1 or claim 8.

Column 14, line 24, "claim 1," should read -- claim 1 or claim 8.

Signed and Sealed this

Sixth Day of March, 2001

Attest:

NICHOLAS P. GODICI

Attesting Officer

Acting Director of the United States Patent and Trademark Office